US012653642B2

(12) United States Patent
Salah et al.

(10) Patent No.: US 12,653,642 B2
(45) Date of Patent: Jun. 16, 2026

(54) METHOD FOR GENERATING A DENTAL IMAGE

(71) Applicant: DENTAL MONITORING, Paris (FR)

(72) Inventors: Philippe Salah, Paris (FR); Thomas Pellissard, Paris (FR); Guillaume Ghyselinck, Cantin (FR); Laura Misrachi, Paris (FR)

(73) Assignee: DENTAL MONITORING, Paris (FR)

( * ) Notice: Subject to any disclaimer, the term of this patent is extended or adjusted under 35 U.S.C. 154(b) by 113 days.

(21) Appl. No.: 17/770,868

(22) PCT Filed: Oct. 21, 2020

(86) PCT No.: PCT/EP2020/079580
§ 371 (c)(1),
(2) Date: Apr. 21, 2022

(87) PCT Pub. No.: WO2021/078778
PCT Pub. Date: Apr. 29, 2021

(65) Prior Publication Data
US 2022/0378548 A1 Dec. 1, 2022

(30) Foreign Application Priority Data

Oct. 22, 2019 (FR) ...................................... 1911793

(51) Int. Cl.
*A61C 7/00* (2006.01)
*A61B 1/24* (2006.01)
*G06T 15/04* (2011.01)
*G06T 19/20* (2011.01)

(52) U.S. Cl.
CPC .............. *A61C 7/002* (2013.01); *G06T 15/04* (2013.01); *G06T 19/20* (2013.01); *A61B 1/24* (2013.01); *G06T 2210/41* (2013.01); *G06T 2219/2004* (2013.01)

(58) Field of Classification Search
None
See application file for complete search history.

(56) References Cited

U.S. PATENT DOCUMENTS

| | | | |
|---|---|---|---|
| 10,945,813 B2 * | 3/2021 | Li | A61C 7/002 |
| 2018/0174367 A1 * | 6/2018 | Marom | G06T 19/006 |
| 2018/0263733 A1 | 9/2018 | Pokotilov et al. | |

FOREIGN PATENT DOCUMENTS

| | | |
|---|---|---|
| CN | 107518952 A | 12/2017 |
| WO | 2018112427 A1 | 6/2018 |

OTHER PUBLICATIONS

International Search Report corresponding to International Application No. PCT/EP2020/079580 dated Dec. 10, 2020, 6 pages.

* cited by examiner

*Primary Examiner* — James A Thompson
(74) *Attorney, Agent, or Firm* — Ronald M. Kachmarik; Cooper Legal Group LLC

(57) ABSTRACT

A method for generating an image of a dental arch of a beneficiary, called "modified image." The method includes, at an acquisition time, acquiring a photo depicting the dental arch, called "original image." The method successively includes processing the original image such that it depicts discriminating information. The method successively includes submitting the original image at the input of a neural network, called "simulation neural network", trained, based on the original image, to simulate, on the original image, the effect of a dental event, in order to obtain the modified image.

13 Claims, 3 Drawing Sheets

[Fig 1]

a) acquire a photo of a dental arch, or "original image"

b) process the original image such that it depicts a contour of the dental arch c) submit the original image to a neural network trained to simulate, on the original image, the effect of a dental event d) process the modified image in order to make it hyper-realistic e) present the modified image and/or select an orthodontic appliance

[Fig 2]

1) acquire a first view of a historical model and process such that it depicts a first contour 2) modify the historical model by simulating a dental event 3) acquire a second view of the historical model and process such that it depicts a second contour, and then create a historical record with the first and second views 4) train a neural network with the historical records

[Fig 3]

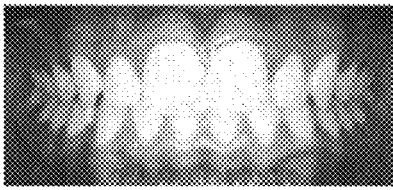
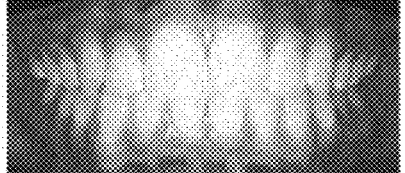

[Fig 4]
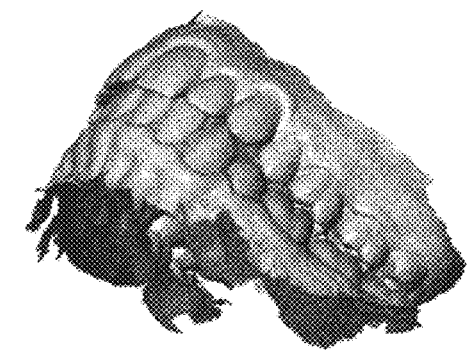
[Fig 5]
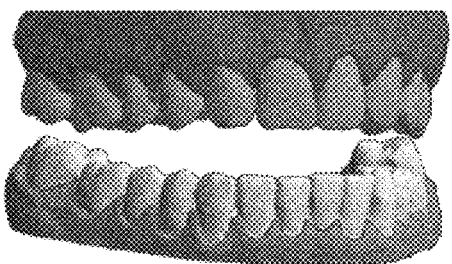
[Fig 6]
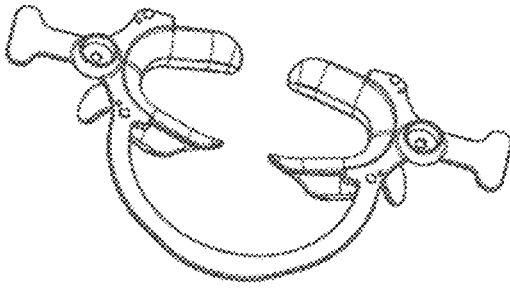
[Fig 7]
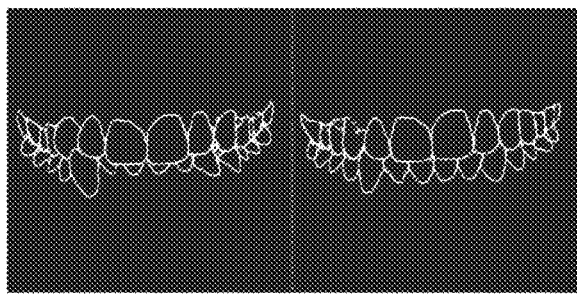

[Fig 8]
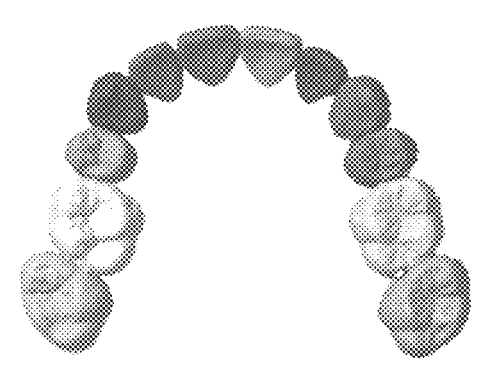

METHOD FOR GENERATING A DENTAL IMAGE

TECHNICAL FIELD

The present invention relates to generating images of dental arches. It relates in particular to a method for realistically visualizing, in an image, the effect of a dental event liable to affect the dental arch of a beneficiary, for example a patient undergoing orthodontic treatment.

PRIOR ART

PCT/EP2019/068558 describes a method in which digital three-dimensional models of dental arches, and in particular scans performed by dental professionals, are deformed so as to simulate (that is to say are adapted so as to artificially reproduce) a dental situation that is anticipated at a past simulation time or that is predicted at a future simulation time. The deformed models are used to create hyper-realistic views equivalent to photos.

People therefore have to visit the orthodontist in order to create models of their dental arches. The field of application of this method is therefore limited.

There is therefore a need for a method for generating dental arch images that simulate the effect of a dental event and that would not require the generation of a model.

One aim of the invention is to address this need.

SUMMARY OF THE INVENTION

According to a first main aspect, the invention relates to a method for generating an image of a dental arch of a beneficiary, called "modified image", said method comprising the following successive steps:

a) at an acquisition time, acquiring a photo depicting said dental arch, called "original image";

b) processing the original image such that it depicts discriminating information, preferably a contour of the dental arch;

c) submitting the original image to a neural network, called "simulation neural network", trained to simulate, on the original image, the effect of a dental event, in order to obtain the modified image;

d) preferably, processing the modified image in order to make it hyper-realistic;

e) preferably, presenting the modified image, preferably at least to the beneficiary and/or to a dental professional; and/or selecting an orthodontic appliance, performed by a computer and/or by the beneficiary and/or by a dental professional, based on the modified image, and then, preferably, manufacturing said orthodontic appliance.

As will be seen in more detail in the remainder of the description, a generation method according to the invention does not require generating a model of the dental arch of the beneficiary. What is noteworthy is that anyone, undergoing treatment or not, is able to obtain a simulation of the effect of the dental event on their teeth, without having to visit the orthodontist.

In particular, the modified image depicts the arch as simulated after application of the dental event. The beneficiary may thus benefit from a simulation allowing them to accurately measure the visual impact of the dental event.

A generation method according to the invention may furthermore comprise one or more of the following optional features:

the dental event is chosen from among a passage of time in the context of an orthodontic or non-orthodontic treatment, in the context of a pathology or in the context of bruxism, fitting of a dental member on the dental arch, a passage of time in the absence of treatment, and combinations of these dental events;

the discriminating information is chosen from the group consisting of contour information, color information, density information, distance information, brightness information, saturation information, information regarding reflections and combinations of this information;

the simulation neural network is trained by way of a training method according to the invention, described below;

the cycle of steps 1) to 4) is repeated, the first observation conditions being modified at the end of each step 4);

in step a), the photo is acquired extra-orally, preferably with a cell phone, the beneficiary preferably wearing a dental retractor;

the method comprises a step d) of processing the modified image in order to make it hyper-realistic, step d) comprising the following steps:

d0) for each photo, called "texturing photo", depicting a dental arch from a set comprising more than 1000 texturing photos, processing the texturing photo, preferably as in step b), so as to obtain an image, called "texturing image", depicting a contour;

d1) creating what is called a "texturing" learning base consisting of records, called "texturing records", each texturing record comprising a texturing photo and the texturing image obtained by processing said texturing photo in step d0);

d2) training a neural network, called "texturing neural network", by way of the texturing learning base;

d3) submitting the modified image to the trained texturing neural network, so as to obtain a hyper-realistic modified image;

the dental event is a passage of time from the acquisition time to a simulation time more than 1 day before or after the acquisition time, and, in step e), the modified image is presented to the beneficiary in order to show them a dental situation determined, that is to say simulated, at said simulation time;

before step c), the dental event is determined by specifying a simulation time, and/or a parameter of a treatment applied to the beneficiary and/or a parameter of an orthodontic appliance worn by the beneficiary, and/or a functional parameter of the beneficiary, and/or an anatomical parameter of the beneficiary other than the positioning parameters of their teeth, and/or an age, or an age bracket, and/or a gender of said beneficiary;

steps a) to e) are repeated in a loop, with original images acquired successively, each cycle lasting less than 5 s, preferably less than 1 s.

According to a second main aspect, the invention relates to a method for training a neural network, said method comprising, for each of a plurality of digital three-dimensional models of "historical" dental arches, called "historical models", the following successive steps 1) to 3):

1) acquiring a first view of the historical model under first observation conditions and, if said first view does not depict discriminating information of the historical dental arch, called "first discriminating information", preferably does not depict a contour of the historical dental arch, called "first contour", processing the first view such that it depicts said first discriminating information, preferably a first contour;

2) modifying the historical model, for example through deformation and/or adding a dental member, so as to reproduce the effect of a dental event on said historical dental arch;

3) acquiring a second view of the historical model under second observation conditions identical to the first observation conditions and, if said second view does not depict said discriminating information of the historical dental arch, called "second discriminating information", in particular if said second view does not depict a contour of the historical dental arch, called "second contour", processing the second view such that it depicts said second discriminating information, preferably a second contour, and creating a historical record with the first and second views;

and then, with all of the historical records created for all of the historical models:

4) introducing said first and second views, respectively, at the input and at the output of the neural network, so as to train said neural network to transform an input view depicting an analysis dental arch into an output view depicting said analysis dental arch after application of said dental event.

Observing the historical model under the same observation conditions makes it possible to very easily obtain perfectly aligned first and second views. No cropping is necessary.

In one embodiment, in step 1), more than 10, more than 100, more than 1000, more than 10 000 first views are acquired under first observation conditions that are different each time, and then, in step 3), for each first view acquired under first observation conditions, a second view is acquired under second observation conditions identical to said first observation conditions, and a historical record is created with said first and second views.

Preferably, the simulation neural network used in step c) is trained with a training method according to the invention.

A generation method and/or a training method according to the invention are at least partially computer-implemented. The invention therefore also relates to:

a computer program comprising program code instructions for executing steps b) to e) of a simulation method according to the invention, and/or for executing steps 1), 3) and 4), and preferably 2) of a training method according to the invention when said program is executed by a computer, a computer medium on which such a program is recorded, for example a memory or a CD-ROM.

Any computer may be contemplated, in particular a telephone, a PC, a server or a tablet.

Definitions

An "orthodontic treatment" is all or part of a treatment intended to modify the configuration of a dental arch.

A "dental member" is understood to mean any device intended to be worn by the dental arch, and in particular an orthodontic appliance, a crown, an implant, a bridge or a veneer.

A "dental situation" defines a set of features relating to an arch of a patient at a time, for example the position of the teeth, their shape, their color, the position of an orthodontic device, etc. at this time.

A "beneficiary" is a person for whom a method according to the invention is implemented, regardless of whether or not this person is undergoing orthodontic treatment.

A "dental professional" is understood to mean any person qualified to provide dental care, including in particular an orthodontist and a dentist.

A "computer" is understood to mean any electronic device with data processing capabilities.

A "retractor", or "dental retractor", is a device intended to push back the lips. It has an upper rim and a lower rim extending around a retractor opening. In the service position, the upper and lower lips of the patient rest on the upper and lower rims, respectively. The retractor is configured so as to elastically space the upper and lower lips from one another so as to leave the teeth visible through the opening. A retractor thus makes it possible to observe the teeth without being hampered by the lips. However, the teeth do not rest on the retractor, meaning that the patient is able, by turning their head relative to the retractor, to modify the teeth that are visible through the opening of the retractor. It may also modify the spacing between the arches. In particular, a retractor does not press on the teeth so as to space the two jaws from one another. Preferably, the retractor comprises ears for spreading the cheeks, thereby making it possible to acquire, through the retractor opening, photos of the vestibular surfaces of the teeth at the back of the mouth, such as molars.

A "model" is understood to mean a digital three-dimensional model. A model consists of a set of voxels.

For the sake of clarity, a distinction is conventionally made between "dividing" an arch model into "elementary models" and "segmenting" an image into "elementary areas". The elementary models and the elementary areas are 3D or 2D depictions, respectively, of an element of a real scene, for example of a tooth.

The "observation conditions" of a model specify the position in space, the orientation in space and the calibration, for example the values of the diaphragm aperture and/or the exposure time and/or the focal length and/or the sensitivity, of a virtual image acquisition device, in relation to this model.

The "calibration" of an acquisition device consists of the set of values of the calibration parameters. A calibration parameter is a parameter intrinsic to the acquisition device (unlike its position and its orientation), the value of which influences the image acquired. For example, the diaphragm aperture is a calibration parameter that modifies the depth of field. The exposure time is a calibration parameter that modifies the luminosity (or the "exposure") of the image. The focal length is a calibration parameter that modifies the viewing angle, that is to say the degree of "zoom". The "sensitivity" is a calibration parameter that modifies the reaction of the sensor of a digital acquisition device to incident light.

An observation of a model, under determined observation conditions, is called a "view".

An "image" is a two-dimensional depiction, formed of pixels, of an arch. A "photo" is therefore a particular image, conventionally in color, taken with a camera. A "camera" is understood to mean any device for taking a photo, including a dedicated camera, a cell phone, a tablet or a computer. A view is another example of an image.

A "photo of an arch", "depiction of an arch", "scan of an arch", "model of an arch", "image of an arch", "view of an arch" or "contour of an arch" is understood to mean a photo, a depiction, a scan, a model, an image, a view or a contour of all or part of said dental arch, preferably of at least 2, preferably at least 3, preferably at least 4 teeth.

A "dental event" is understood to mean an event liable to modify a dental arch, for example the wearing of an orthodontic appliance or the simple passage of time.

"Discriminating information" is characteristic information that is able to be extracted from an image ("image feature"), conventionally through computer processing of this image.

Discriminating information may exhibit a variable number of values. For example, contour information may represent a probability of a pixel belonging to a contour, and adopt for example a value between 0 and 255, 0 being a very low probability of the pixel belonging to a contour and 255 a very high probability. In one embodiment, the discriminating information is thresholded, that is to say that only the discriminating information that exceeds a predetermined threshold value is depicted. For example, in the above example of contour information, only values greater than 200 are depicted. Brightness information may adopt a great many values. Image processing makes it possible to extract and quantify the discriminating information.

The discriminating information may be depicted in an image, sometimes called a "map". A map is thus the result of processing an image in order to reveal the discriminating information. For example, the contour of the teeth and gums may be the depiction of the contour information from an original image. The depiction of a contour is therefore the depiction of the contour information in the form of an image.

A "contour" is a line or a set of lines that delimit(s) an object and preferably the elements forming this object. For example, the contour of a dentition may be a line that defines the outer limits of this dentition. Preferably, it furthermore comprises the lines that define the boundaries between adjacent teeth. Preferably, the contour of the dentition therefore consists of all of the contours of the teeth that form this dentition.

A contour depicted in an image may be complete, and therefore closed on itself, or incomplete.

The contour of a dental arch preferably depicts the contour of the dentition of this arch and, preferably, the contours of each tooth depicted, called "elementary contours".

In a method according to the invention, the processing operations applied to images are preferably configured so as to reveal, preferably isolate the same contours, preferably contours comprising, preferably substantially consisting of, all of the elementary contours of the teeth depicted, as in FIG. 7.

A "neural network" or "artificial neural network" is a set of algorithms well known to those skilled in the art. To be operational, a neural network has to be trained by a learning process called "deep learning", from a learning base.

A "learning base" is a base of computer records suitable for training a neural network. The quality of the analysis performed by the neural network depends directly on the number of records in the learning base. Conventionally, the learning base contains more than 10 000 records.

The training of a neural network is adapted to the desired aim, and does not pose any particular difficulty to those skilled in the art.

Training a neural network consists in confronting it with a learning base containing information about the two types of object that the neural network has to learn to "match", that is to say connect with one another.

The training may be performed from a "paired" learning base or learning base "with pairs", consisting of "pair" records, that is to say each comprising a first object of a first type for the input of the neural network, and a second corresponding object, of a second type, for the output of the neural network. It is also said that the input and the output of the neural network are "paired". Training the neural network with all of these pairs teaches it to provide, from any object of the first type, a corresponding object of the second type.

For example, each record in the learning base may comprise a first view of a model of a dental arch and a second view of this model, after a dental event has taken place. After having been trained with this learning base, the neural network will be able to transform a view of a model of a dental arch into a view of this model that is modified so as to simulate the effect of a said dental event.

The article "Image-to-Image Translation with Conditional Adversarial Networks" by Phillip Isola Jun-Yan Zhu, Tinghui Zhou, Alexei A. Efros, Berkeley AI Research (BAIR) Laboratory, UC Berkeley, illustrates the use of a paired learning base.

In the present description, the qualifiers "historical", "original", "texturing", "simulation" and "analysis" are used for the sake of clarity.

"Comprising" or "having" or "exhibiting" are to be interpreted non-restrictively unless indicated otherwise.

BRIEF DESCRIPTION OF THE FIGURES

Additional features and advantages of the invention will become further apparent upon reading the following detailed description and from studying the attached drawing, in which:

FIG. 1 schematically shows the various steps of one preferred embodiment of an image generation method according to the invention;

FIG. 2 schematically shows the various steps of one preferred embodiment of a training method according to the invention;

FIG. 3 shows one example of a photo acquired in step a), and of the modified image obtained by way of a method according to the invention trained with records such as the one of FIG. 7;

FIG. 4 shows one example of a model of a dental arch;

FIG. 5 shows a view of a model of a dental arch;

FIG. 6 shows one example of a retractor;

FIG. 7 shows one example of a record used to train the simulation neural network in order to simulate the event "orthodontic treatment with an orthodontic appliance with an arch wire and brackets", the left-hand and right-hand images being introduced at the input and at the output of the simulation neural network, respectively;

FIG. 8 shows one example of a model divided into tooth models, the other elements of the arch not being shown.

DETAILED DESCRIPTION

The following detailed description is that of preferred embodiments, but is not limiting.

In particular, it describes the use of discriminating information, which is contour information. The discriminating information could however be of another type.

Training a Neural Network

The method for training a neural network according to the invention preferably comprises steps 1) to 4) (FIG. 1).

Steps 1) to 3) of this method advantageously make it possible to increase the number of records used in step 4).

Prior to these steps, one, preferably several, preferably more than 100, preferably more than 1000, preferably more than 10 000 historical models are generated.

Each historical model depicts a dental arch of what is called a "historical" individual.

The historical model may be prepared from measurements taken on the teeth of the historical individual or on a cast of their teeth, for example a plaster cast.

The historical model is preferably obtained from a real situation, preferably created with a 3D scanner. Such a model, called a "3D" model, may be observed from any angle (FIG. 4).

Preferably, the historical model is divided. In particular, preferably, for each tooth, a model of said tooth, or "tooth model", is defined on the basis of the historical model.

The division of a historical model of a dental arch into tooth models is a conventional operation by way of which the model of the arch is divided in order to delimit the depiction of one or more of the teeth in the model (FIG. 8).

The historical model may be divided manually by an operator, using a computer, or be divided automatically, by a computer, preferably by implementing a deep learning device, preferably a neural network. In particular, the tooth models may be defined as described for example in international application PCT/EP2015/074896.

In the historical model, a tooth model is preferably delimited by a gingival edge, which may be broken down into an inner gingival edge (on the side of the inside of the mouth with respect to the tooth), an outer gingival edge (facing the outside of the mouth with respect to the tooth) and two lateral gingival edges.

Similarly, it is possible, based on the historical model, to define elementary models other than the tooth models, and in particular models for the tongue, and/or the mouth, and/or the lips, and/or the jaws, and/or the gums, and/or a dental member, in particular an orthodontic appliance.

In one embodiment, the historical model is theoretical, that is to say does not correspond to a real situation. In particular, the historical model may be created by assembling a set of tooth models chosen from a digital library. The arrangement of the tooth models is determined such that the historical model is realistic, that is to say corresponds to a situation that could have been encountered in an individual. In particular, the tooth models are arranged in an arc, depending on their nature, and oriented realistically. Using a theoretical historical model advantageously makes it possible to simulate dental arches exhibiting rare features.

A historical model preferably provides information regarding the positioning of the teeth with an error of less than $\frac{5}{10}$ mm, preferably less than $\frac{3}{10}$ mm, preferably less than $\frac{1}{10}$ mm.

A historical model is for example of the .stl or .Obj, .DXF 3D, IGES, STEP, VDA or points clouds type. Advantageously, such a model, called a "3D" model, may be observed from any angle.

For each historical model, steps 1) to 4) are taken.

In step 1), a first view of the historical model is acquired under first observation conditions, that is to say by virtually placing a virtual image acquisition device under these first observation conditions, and then by acquiring the first view with this device configured in this way.

The first view is preferably an extra-oral view, for example a view corresponding to a photo that might have been taken facing the patient, preferably with a retractor.

FIG. 6 shows one example of a retractor.

If the first view does not depict a contour, or does not make it possible to identify same, a processing operation is applied to isolate the contour, preferably the contour of the teeth.

FIG. 5 shows one example of a first view, before processing to isolate the contour.

The left-hand part of FIG. 7 shows one example of a first view, after processing to isolate the contour of the teeth.

In step 2), the historical model is modified to simulate the effect of a dental event.

Modifying the historical model may in particular consist in displacing, deforming or removing one or more teeth ("tooth model"), and/or the gums, and/or one or both jaws, and/or an orthodontic appliance in the elementary model.

The modification may be performed manually, by an operator, preferably by a dental professional, more preferably an orthodontist, preferably using a computer allowing them to view the model currently being modified.

Step 2) leads to a historical model that depicts a theoretical dental situation.

This model may advantageously simulate dental situations for which measurements are not available. In particular, it is possible to create historical models corresponding to different stages of a rare pathology.

In step 3), a view of the historical model modified in step 2), called "second view", is acquired under the same observation conditions of the historical model as those that made it possible to acquire the first view. In other words, the depictions, in the first and second views, of the teeth that have not moved between steps 1) and 3) may be perfectly superposed, that is to say "aligned".

If the second view does not depict a contour, or does not make it possible to identify same, a processing operation is applied to isolate the contour, preferably the contour of the teeth.

The right-hand part of FIG. 7 shows one example of a second view, after processing to isolate the contour of the teeth. Comparing the left-hand and right-hand parts of FIG. 7 makes it possible to visualize the effect of the dental event, in this case the effect of orthodontic treatment by way of a appliance with an arch wire and brackets.

A pair, or "historical record", is thus generated, consisting of the first view and the associated second view representing the application of the dental event to the arch depicted in the first image. The historical record is added to the historical learning base.

FIG. 2 shows one example of a historical record.

In one embodiment, in step 1), more than 10, more than 100, more than 1000, more than 10 000 first views are acquired under first observation conditions that are different each time, and then, in step 3), for each first view acquired under first observation conditions, a second view is acquired under second observation conditions identical to said first observation conditions, and a historical record is created with said first and second views.

This procedure is equivalent to performing, after step 3), more than 10, more than 100, more than 1000, more than 10 000 cycles of steps 1) and 3), without step 2), by modifying the first observation conditions in each cycle. In other words, first and second views are acquired by moving around the historical model, in particular by rotating around the historical model, and/or by approaching or moving away, and/or by modifying the calibration of the virtual acquisition device for acquiring the first and second views.

The invention thus advantageously makes it possible to increase the number of historical records with one and the same historical model.

Next, the historical model is changed and there is a return to step 1).

A historical learning base is thus formed, comprising preferably more than 5000, preferably more than 10 000, preferably more than 30 000, preferably more than 50 000, preferably more than 100 000 historical records.

In step 4), the neural network is then trained with the historical learning base. Such training is well known to those skilled in the art.

It conventionally consists in providing all of said first views at the input of the neural network and all of said second views at the output of the neural network, by establishing, for each first view, a bijective relationship with the corresponding second view, that is to say belonging to the same record.

Through this training, the neural network learns to transform an input view depicting a contour of an analysis dental arch (such as the first view) into an output view depicting the same arch, but after the dental event has taken place.

The neural network may in particular be chosen from among networks specializing in image generation, for example:

Cycle-Consistent Adversarial Networks (2017)
Augmented CycleGAN (2018)
Deep Photo Style Transfer (2017)
FastPhotoStyle (2018)
pix2pix (2017)
Style-Based Generator Architecture for GANs (2018)
SRGAN (2018).

The above list is not limiting.

The neural network trained in this way may be used to simulate the effect of a dental event on a dental arch depicted in a simple photo, in line with steps a) to e) described below. The neural network is then referred to as a "transformation neural network".

Simulation of a Dental Event

In step a), an original image is created by acquiring a photo with a camera, preferably chosen from among a cell phone, what is called a "connected" camera, what is called a "smartwatch", a tablet or a fixed or portable personal computer, comprising a photo acquisition system. Preferably, the camera is a cell phone.

Preferably, when acquiring the photo, the camera is spaced from the dental arch by more than 5 cm, more than 8 cm, or even more than 10 cm, thereby avoiding the condensation of water vapor on the camera optics and facilitating focusing. Furthermore, preferably, the camera, in particular the cell phone, is not provided with any specific optics for acquiring photos, which is possible in particular due to the spacing from the dental arch during the acquisition.

To facilitate the acquisition of the photo, the retractor and the camera are preferably fixed on one and the same support, thereby making it possible to fix their relative positions. Preferably, the support is portable and should be held in the hand of the beneficiary when taking the photo.

Preferably, the photo is in color, preferably in real color.

Preferably, the photo is acquired by the beneficiary, preferably without using a support for immobilizing the camera, and in particular without a tripod.

The photo is preferably an extra-oral view, for example a view corresponding to a photo that might have been taken facing the patient, preferably with a retractor.

The retractor may have the features of conventional retractors.

In step b), the processing of the original image aims to highlight, or even isolate, discriminating information contained in the original image. Using discriminating information considerably improves the efficiency of the neural network implemented in step c).

Preferably, the original image is processed so as to reveal and preferably isolate a contour.

Preferably, the original image is processed so as to substantially no longer depict anything but a contour. Preferably, the contour comprises the elementary contour of each tooth depicted, or even consists of all of the elementary contours of the teeth.

The contour may also comprise, or even consist of only the contour of all of the teeth depicted. However, this embodiment is not preferred.

Those skilled in the art know how to process a photo or a view to isolate a contour. Such processing comprises for example applying well-known masks or filters, which come with image processing software. Such processing operations make it possible for example to detect high-contrast regions.

These processing operations comprise in particular one or more of the following known and preferred methods:

application of a Canny filter, in particular to search for contours using the Canny algorithm;

application of a Sobel filter, in particular to calculate derivatives by way of the extended Sobel operator;

application of a Laplace filter, to calculate the Laplacian of an image;

detection of blobs in an image ("Blobdetector");

application of a "Threshold" to apply a fixed threshold to each element of a vector;

resizing, using relationships between pixel areas ("Resize (Area)") or bi-cubic interpolations on the pixel environment;

erosion of the image by way of a specific structuring element;

dilation of the image by way of a specific structuring element;

image correction, in particular using regions in the vicinity of the restored area;

application of a bilateral filter;

application of Gaussian blurring;

application of an Otsu filter, to search for the threshold that minimizes variance between classes;

application of an A*filter, to search for a path between points;

application of an "Adaptive Threshold" to apply an adaptive threshold to a vector;

application of a histogram equalization filter to an image in grayscale in particular;

blur detection ("BlurDetection"), to calculate the entropy of an image using its Laplacian;

detection of contours ("FindContour") of a binary image;

filling with color ("FloodFill"), in particular to fill a connected element with a determined color.

The following non-limiting methods, although they are not preferred, may also be implemented:

application of a "MeanShift" filter, so as to find an object on a projection of the image;

application of a "CLAHE" filter, which stands for "Contrast Limited Adaptive Histogram Equalization";

application of a "Kmeans" filter, to determine the center
of clusters and of groups of samples around clusters;

application of a DFT filter, so as to perform a direct or
inverse discrete Fourier transform on a vector;

calculation of moments;

application of a "HuMoments" filter to calculate invariant
Hu invariants;

calculation of the integral of an image;

application of a Scharr filter, making it possible to cal-
culate a derivative of the image by implementing a
Scharr operator;

searching for the convex hull of points ("ConvexHull");

searching for convexity points of a contour ("Convexity-
Defects");

comparison of shapes ("MatchShapes");

checking whether points are in a contour ("PointPolygon-
Test");

detection of Harris corners ("CornerHarris");

searching for minimum eigenvalues in matrices of gradi-
ents, in order to detect corners ("CornerMinEigenVal");

application of a Hough transform to find circles in a
grayscale image ("HoughCircles");

"Active contour modeling" (plotting the contour of an
object from a potentially "noisy" 2D image);

calculating a field of forces, called GVF ("gradient vector
flow"), in part of the image;

cascade classification ("CascadeClassification").

The processing may also be performed by way of a neural
network trained for this purpose. This neural network is
preferably chosen from among networks specializing in the
location and detection of objects in an image, "Object
Detection Networks", for example

R-CNN (2013)

SSD (Single Shot MultiBox Detector: Object Detection
network), Faster R-CNN (Faster Region-based Convo-
lutional Network method: Object Detection network)

Faster R-CNN (2015)

SSD (2015).

The determination of tooth contours may be optimized in
line with the teachings in PCT/EP2015/074900 or
FR1901755.

Step b) advantageously makes it possible to obtain an
image able to be processed very easily by a neural network.

In step c), the original image from step b) is presented at
the input of the simulation neural network. The simulation
neural network then modifies the original image to simulate
the effect of the dental event on the dental arch depicted
therein.

Advantageously, only the original image needs to be
presented at the input of the simulation neural network. No
three-dimensional information, for example a three-dimen-
sional digital model, needs to be presented to the simulation
neural network. Moreover, the entire original image may be
submitted to the simulation neural network. It is not neces-
sary to isolate an element of this image. The simulation
neural network generates a new image from the original
image. In other words, no part of the original image is
simply copied. Any part of the original image is liable to be
modified when generating the new image.

Preferably, the simulation neural network has been trained
beforehand by providing it with the following:

at input, a set of "input" images each depicting the
discriminating information of a respective "input" real-
istic image depicting a respective dental arch, for
example of a photo of this arch or of a hyper-realistic
view of a three-dimensional model of this arch, and at output, a set of "output" images, each output image
being associated with an input image and depicting the
discriminating information of a respective "output"
realistic image depicting the dental arch depicted in the
associated "input" hyper-realistic image, but after a
dental event has taken place, the output realistic image
being for example a photo of this arch or a hyper-
realistic view of a three-dimensional model of this arch.

"Realistic" is understood to mean that the depiction of the
arch is similar to that able to be observed by a person with
the naked eye, in reality.

Through this training, the simulation neural network
learns to transform an input image into an output image, and
therefore learns to simulate the dental event.

Preferably, the discriminating information depicted in the
input and output images is a contour.

The simulation neural network that is used may in par-
ticular have been trained in line with steps 1) to 4).

In step d), which is optional but preferred, the modified
image obtained at the end of step c) is modified such that it
is hyper-realistic, that is to say it appears to be a photo.

All means for making the modified image hyper-realistic
are possible.

Some image texturing techniques are described in the
article by Zhu, Jun-Yan, et "Unpaired image-to-image trans-
lation using cycle-consistent adversarial networks."

Preferably, use is made of what is called a "texturing"
neural network trained to make images depicting contours
hyper-realistic, such as the modified image, and preferably
comprising steps d0) to d3) below.

The texturing neural network may be chosen from the list
of neural networks presented above for the neural network
implemented in the training method according to the inven-
tion. The texturing neural network may in particular be
chosen from among networks specializing in image genera-
tion, for example:

Cycle-Consistent Adversarial Networks (2017)

Augmented CycleGAN (2018)

Deep Photo Style Transfer (2017)

FastPhotoStyle (2018)

pix2pix (2017)

Style-Based Generator Architecture for GANs (2018)

SRGAN (2018).

However, it is not limited to this list.

In step d0) for each photo, called "texturing photo",
depicting a dental arch from a set comprising more than
1000 texturing photos, the texturing photo is processed, preferably as in step b),
so as to obtain an image, called "texturing image",
depicting a contour.

In step d1), what is called a "texturing" learning base is
created, consisting of what are called "texturing" records,
each texturing record comprising:

a texturing photo depicting a dental arch, and the texturing image obtained, in a step d0) prior to step
d1), by processing said texturing photo in step d0).

In step d2), the texturing neural network is trained by way
of the texturing learning base. Such training is well known
to those skilled in the art.

It conventionally consists in providing all of said textur-
ing images at the input of the texturing neural network and
all of said texturing photos at the output of the texturing
neural network, while informing the texturing neural net-
work of the texturing photo that corresponds to each tex-
turing image.

Through this training, the texturing neural network learns to transform an image depicting a dental arch contour, such as the modified image, into a hyper-realistic image.

In step d3), the modified image is submitted to the trained texturing neural network. The texturing neural network transforms it into a hyper-realistic image.

FIG. 3 shows one example of a photo acquired in step a) (on the left) and of a modified image obtained at the end of step d) (on the right). It is possible to observe the effect of the dental event on the position of certain teeth.

In step e), the modified image, preferably made hyper-realistic, may be presented, in particular to the beneficiary, preferably on a screen, preferably on a screen of a cell phone, a tablet, a portable computer, or a virtual reality headset. The screen may also be the glass of a mirror.

The generation method and the training method are implemented by way of a computer. Conventionally, a computer comprises in particular a processor, a memory, a human-machine interface, conventionally comprising a screen, a module for communication via the Internet, via Wi-Fi, via Bluetooth® or via the telephone network. Software configured so as to implement the method of the invention under consideration is loaded into the memory of the computer.

The computer may also be connected to a printer.

In one embodiment, the human-machine interface makes it possible to communicate the following to the computer:
a simulation time when the dental event comprises a passage of time between the acquisition time and said simulation time, and/or
a parameter of a treatment applied to the beneficiary; and/or
a parameter of an orthodontic appliance worn by the beneficiary, for example relating to the class and/or to the conformation of the orthodontic appliance; and/or
a functional parameter of the beneficiary, in particular a neurofunctional parameter, such as ease of breathing, swallowing or closing the mouth; and/or
an anatomical parameter of the beneficiary other than the positioning parameters of their teeth, such as the arrangement and/or the structure of bone tissue (in particular of the jaws) and/or of alveodental tissue and/or of soft tissue (in particular the gums and/or the frenulum and/or the tongue and/or the cheeks); and/or
the age, or an age bracket, and/or the gender of said beneficiary.

It is thus possible for the computer to choose a simulation neural network trained accordingly.

For example, it is possible to choose a simulation neural network trained to simulate movement of teeth with an orthodontic appliance with an arch wire and brackets, for a man aged 30 to 40, having "normal" bone tissue.

The method makes it possible in particular to simulate the effect of various orthodontic treatments, thereby facilitating the choice of the treatment most suited to the needs or wishes of the beneficiary.

Preferably, the human-machine interface comprises a screen having a field for entering the simulation time.

In one embodiment, the human-machine interface makes it possible to selectively display or not display an orthodontic appliance worn by the beneficiary on the screen.

EXAMPLES

Simulation of a Past or Future Dental Situation

In one embodiment, the beneficiary takes the original image, for example with their cell phone (step a)), and a computer, integrated into the cell phone or with which the cell phone is able to communicate, implements steps b) to e). The modified image is preferably presented on the screen of the cell phone.

Preferably, the computer is integrated into the cell phone, thereby allowing the beneficiary to implement the generation method according to the invention completely autonomously.

The beneficiary may thus very easily request a simulation of a dental situation, without even having to move, based on one or preferably several photos of their teeth.

In particular, the dental situation may be simulated at a past or future simulation time. The simulation time may for example be before or after the acquisition time of the original image, for example more than 1 day, 10 days or 100 days before or after the acquisition time.

In one particular case, the dental event is the passage of time in the context of a treatment, for example an orthodontic treatment during which the beneficiary wears an orthodontic appliance.

Preferably, the method comprises a step d). The modified image that is presented then appears as a photo that would have been taken at the simulation time. It may be presented to the beneficiary in order to show them for example their future or past dental situation, and thus motivate them to follow the treatment.

In one particular case, the dental event is the passage of time in the context of an orthodontic treatment during which the beneficiary does not comply with medical recommendations, for example does not wear their orthodontic appliance correctly. The presentation of a photorealistic modified image thus makes it possible to visualize the effect of incorrect compliance.

A generation method according to the invention may be used in particular to simulate:
the effect of one or more orthodontic appliances on the teeth of the beneficiary, in particular in order to choose the one that best suits said beneficiary;
the effect of temporarily or definitively stopping an ongoing treatment;
the effect of applying an instruction;
the effect of a therapeutic or non-therapeutic treatment.

In particular, the method may be used, in particular for educational purposes, to visualize the effect of modifying the frequency and/or the duration and/or the technique of brushing the teeth, or the effect of a delay in changing an orthodontic splint and/or a delay in making an appointment with the dental professional.

Dynamic Simulation

In one embodiment, steps a) to e) are repeated in a loop, with original images acquired successively. Preferably, each cycle lasts less than 5 s, preferably less than 2 s, preferably less than 1 s. In step a), a camera is preferably used.

The beneficiary may for example see the modified images on a mirror equipped with a camera, in which they look at themselves. Preferably, the modified images are presented in a manner aligned with the images reflected by the mirror, that is to say that the beneficiary sees the modified images as though they were obtained by reflection. They therefore have the impression of observing themselves at the simulation time.

Preferably, between two cycles of steps a) to e), it is possible to modify the simulation time, for example by modifying the position of a cursor shown on the screen. Preferably, the screen is a touch screen and the simulation time is modified through interaction, preferably through swiping, of a finger on said screen.

Event with an Instantaneous Effect

In one particular case, the dental event has an immediate effect that it is desired to visualize.

For example, the dental event is the fitting of an orthodontic appliance. The method thus makes it possible to integrate, into the original image, a depiction of an orthodontic appliance, or to modify an orthodontic appliance depicted in the original image, or to remove an orthodontic appliance depicted in the original image, without modifying the position of the teeth.

The simulation neural network is trained to create a modified image from the original image provided thereto. This method is therefore completely different from a method in which for example an element, for example a depiction of an existing orthodontic appliance, is added to an image. Indeed, in order to integrate a depiction of an orthodontic appliance into the original image, the simulation neural network creates this depiction. This depiction is therefore not the reproduction of a real orthodontic appliance or a three-dimensional model of a real orthodontic appliance, but is generated artificially by the simulation neural network, at the same time as the rest of the image.

Surprisingly, the depiction of the orthodontic appliance is highly realistic and allows a good simulation for the beneficiary. In particular, training the simulation neural network teaches it to depict the orthodontic appliance in the context of the original image, with the corresponding contrast, sharpness, shadows and reflections. The simulation is therefore far more realistic than simply adding a pre-existing depiction of an orthodontic appliance to an image depicting the dental arch.

The modification of the original image by the neural network may lead to modifications to areas of the original image other than the area depicting the orthodontic appliance. These differences, which could be detrimental if the modified image were to be used to intervene on the teeth, for example to guide a dentist during a drilling operation, are not detrimental when the modified image is intended to be presented to the beneficiary. The performance of neural networks may even make it substantially impossible to detect a difference outside the area in which the orthodontic appliance has been depicted.

As is now clearly apparent, the invention allows a beneficiary to simulate the effect of a dental event on the teeth of their dental arches, without them having to perform a scan of this dental arch. In one preferred embodiment, anyone equipped with a cell phone may advantageously perform such a simulation.

Of course, the invention is not limited to the embodiments described above and shown.

In particular, the beneficiary is not limited to a human being. A method according to the invention may be used for another animal.

Moreover, the training method does not necessarily comprise steps 1) to 4), but they are preferred.

A neural network, in particular the simulation neural network, may for example be trained by implementing a method comprising, for a set of individuals comprising preferably more than 100, preferably more than 1000, preferably more than 10 000 individuals, the following steps:

1') acquiring a photo of a dental arch of an individual and processing said photo so as to obtain a first image depicting a contour of the dental arch depicted in the photo;

2') generating a digital three-dimensional model depicting said dental arch after the dental event has taken place;

3') acquiring a view of said model framed with the photo and, if said view does not depict a contour, processing the view such that it depicts a contour of the depicted dental arch;

and then, with all of the first images and views acquired for all of the individuals:

4') introducing said photos and views, respectively, at the input and at the output of the neural network, so as to train said neural network to transform an input view depicting an analysis dental arch into an output view depicting said analysis dental arch after application of said dental event.

In step 2'), the generation of the model depicting the dental arch after the dental event has taken place may be the result of the generation of a model before the dental event has taken place, for example substantially at the same time as that at which the photo was acquired (step 1')), and then the simulation of the dental event on said model, as described for step 2).

In step 3'), the view should be framed with the photo. Preferably, model observation conditions that correspond best ("best fit") to the photo acquisition conditions are sought. In other words, what are sought are a position, an orientation and a calibration of a virtual acquisition device that allow the model to be observed with a view in which the depiction of the teeth that have not moved during the dental event is able to be superposed in a manner aligned with the depiction of said teeth in the photo.

The invention claimed is:

1. A non-transitory computer medium storing computer-program instructions for executing the steps of a method for generating an image of a dental arch of a beneficiary, called "modified image", said method comprising the following successive steps:

b) processing a photo depicting said dental arch such that it depicts discriminating information, said photo being called "original image" and being acquired at an acquisition time;

c) submitting the original image at the input of a neural network, called "simulation neural network", trained to proceed, from the original image, to a simulation on the original image, so that, at output of said simulation neural network, the obtained modified image depicts the dental arch after a dental event;

wherein no three dimensional digital model is presented to the simulation neural network;

wherein the simulation neural network is trained by way of a training method comprising, for each of a plurality of digital three-dimensional models of "historical" dental arches, called "historical models", the following successive steps:

1) Acquiring a first view of the historical model under first observation conditions and, if said first view does not depict discriminating information of the historical dental arch, called "first discriminating information", processing the first view such that it depicts said first discriminating information;

2) modifying the historical model, so as to reproduce the effect of said dental event on said historical dental arch;

3) acquiring a second view of the historical model under second observation conditions identical to the first observation conditions and, if said second view does not depict said discriminating information of the historical dental arch, called "second discriminating information", processing the second view such that it depicts said second discriminating information; and then, with all of the first and second views acquired for all of the historical models:

4) Introducing said first and second views, respectively, at the input and at the output of the simulation neural network, so as to train said simulation neural network to transform an input view depicting an analysis dental arch into an output view depicting said analysis dental arch after application of said dental event.

2. The non-transitory computer medium as claimed in claim 1, wherein the discriminating information is chosen from the group consisting of contour information, color information, density information, distance information, brightness information, saturation information, information regarding reflections and combinations of this information.

3. The non-transitory computer medium as claimed in claim 2, wherein the depiction of the discriminating information is a contour of the dental arch.

4. The non-transitory computer medium as claimed in claim 1, wherein the simulation neural network is trained by way of a training method comprising, for each of a plurality of digital three-dimensional models of "historical" dental arches, called "historical models", the following successive steps:

1) Acquiring a first view of the historical model under first observation conditions and, if said first view does not depict a contour of the historical dental arch, called "first contour", processing the first view such that it depicts a first contour;

2) modifying the historical model, so as to reproduce the effect of said dental event on said historical dental arch;

3) Acquiring a second view of the historical model under second observation conditions identical to the first observation conditions and, if said second view does not depict a contour of the historical dental arch, called "second contour", processing the second view such that it depicts a second contour;

and then, with all of the first and second views acquired for all of the historical models:

4) Introducing said first and second views, respectively, at the input and at the output of the simulation neural network, so as to train said simulation neural network to transform an input view depicting an analysis dental arch into an output view depicting said analysis dental arch after application of said dental event.

5. The non-transitory computer medium as claimed in claim 1, wherein in step 1), more than 10 first views are acquired under first observation conditions that are different each time, and then, in step 3), for each first view acquired under first observation conditions, a second view is acquired under second observation conditions identical to said first observation conditions, and a historical record is created with said first and second views.

6. The non-transitory computer medium as claimed in claim 1, wherein, in step b), the photo is acquired extraorally, with a cell phone, the beneficiary wearing a dental retractor.

7. The non-transitory computer medium as claimed in claim 1, comprising a step d) of processing the modified image in order to make it hyper-realistic, step d) comprising the following steps:

d0) for each photo, called "texturing photo", depicting a dental arch from a set comprising more than 1000 texturing photos, processing the texturing photo, preferably as in step b), so as to obtain an image, called "texturing image", depicting a contour;

d1) creating what is called a "texturing" learning base consisting of records, called "texturing records", each texturing record comprising a texturing photo and the texturing image obtained by processing said texturing photo in step do);

d2) training a neural network, called "texturing neural network", by way of the texturing learning base;

d3) submitting the modified image to the trained texturing neural network, so as to obtain a hyper-realistic modified image.

8. The non-transitory computer medium as claimed in claim 1, wherein, before step c), the dental event is determined by specifying a simulation time, and/or a parameter of a treatment applied to the beneficiary and/or a parameter of an orthodontic appliance worn by the beneficiary, and/or a functional parameter of the beneficiary, and/or an anatomical parameter of the beneficiary other than the positioning parameters of their teeth, and/or an age, or an age bracket, and/or a gender of said beneficiary.

9. The non-transitory computer medium as claimed in claim 1, wherein, in step c), only the original image is submitted at the input of the simulation neural network.

10. The non-transitory computer medium as claimed in claim 1, comprising, after the step c), a step d) of processing the modified image in order to make it hyper-realistic and/or a step e) of presenting the modified image; and/or selecting an orthodontic appliance based on the modified image.

11. The non-transitory computer medium as claimed in claim 10, wherein the dental event is a passage of time from the acquisition time to a simulation time more than 1 day before or after the acquisition time, and wherein, in step e), the modified image is presented to the beneficiary in order to show them a dental situation determined at said simulation time.

12. The non-transitory computer medium as claimed in claim 10, wherein steps step b) to e) are repeated in a loop, with original images acquired successively, each cycle lasting less than 5 s.

13. The non-transitory computer medium as claimed in claim 1, wherein the dental event is chosen from among a passage of time in the context of an orthodontic or non-orthodontic treatment, in the context of a pathology or in the context of bruxism, fitting of a dental member on the dental arch, a passage of time in the absence of treatment, and combinations of these dental events.

\* \* \* \* \*